(12) United States Patent
Chase et al.

(10) Patent No.: US 8,668,675 B2
(45) Date of Patent: Mar. 11, 2014

(54) WEARABLE DRUG DELIVERY DEVICE HAVING SPRING DRIVE AND SLIDING ACTUATION MECHANISM

(75) Inventors: Kent B. Chase, Sun Prairie, WI (US); Garrick D. S. Smith, Madison, WI (US)

(73) Assignee: FluGen, Inc., Madison, WI (US)

( * ) Notice: Subject to any disclaimer, the term of this patent is extended or adjusted under 35 U.S.C. 154(b) by 0 days.

(21) Appl. No.: 13/288,266

(22) Filed: Nov. 3, 2011

(65) Prior Publication Data

US 2012/0109066 A1 May 3, 2012

Related U.S. Application Data

(60) Provisional application No. 61/409,824, filed on Nov. 3, 2010.

(51) Int. Cl.
*A61M 5/00* (2006.01)
(52) U.S. Cl.
USPC ............................. 604/187; 604/180; 604/185
(58) Field of Classification Search
CPC ........................................................ A61M 5/00
USPC .......... 604/134, 136, 137, 173, 180, 185, 187
See application file for complete search history.

(56) References Cited

U.S. PATENT DOCUMENTS

| | | | |
|---|---|---|---|
| 3,922,328 A | 11/1975 | Johnson | |
| 4,111,202 A | 9/1978 | Theeuwes | |
| 4,190,411 A | 2/1980 | Fujimoto | |
| 4,203,440 A | 5/1980 | Theeuwes | |
| 4,299,220 A | 11/1981 | Dorman | |
| 4,327,725 A | 5/1982 | Cortese et al. | |
| 4,449,983 A | 5/1984 | Cortese et al. | |
| 4,551,139 A | 11/1985 | Plaas et al. | |
| 4,559,038 A | 12/1985 | Berg et al. | |
| 4,595,583 A | 6/1986 | Eckenhoff et al. | |
| 4,624,847 A | 11/1986 | Ayer et al. | |
| 4,624,848 A | 11/1986 | Lee | |
| 4,650,469 A | 3/1987 | Berg et al. | |
| 4,655,767 A | 4/1987 | Woodard et al. | |
| 4,663,149 A | 5/1987 | Eckenhoff et al. | |
| 4,675,174 A | 6/1987 | Eckenhoff | |
| 4,723,958 A | 2/1988 | Pope et al. | |

(Continued)

FOREIGN PATENT DOCUMENTS

WO    WO 2007/007128    1/2007

OTHER PUBLICATIONS

International Search Report and Written Opinion for PCT Application No. PCT/US2011/020113, mail date Sep. 20, 2011, 14 pages.

(Continued)

*Primary Examiner* — Nicholas Lucchesi
*Assistant Examiner* — Gerald Landry, II
(74) *Attorney, Agent, or Firm* — Reinhart Boerner Van Deuren s.c.

(57) ABSTRACT

A drug delivery device is provided. The drug delivery device includes a drug reservoir in fluid communication with a microneedle array. The drug delivery device has a sliding actuation mechanism that may be activated by a button or lever. Actuation of the drug delivery device inserts the microneedle array into the skin of a subject and causes a piston to compress the drug reservoir, thereby delivering the drug through the microneedle array to the subject.

10 Claims, 13 Drawing Sheets

(56) References Cited

U.S. PATENT DOCUMENTS

| | | |
|---|---|---|
| 4,772,474 A | 9/1988 | Eckenhoff et al. |
| 4,781,714 A | 11/1988 | Eckenhoff et al. |
| 4,863,456 A | 9/1989 | Stephens et al. |
| 4,948,592 A | 8/1990 | Ayer et al. |
| 4,963,141 A | 10/1990 | Eckenhoff |
| 5,000,957 A | 3/1991 | Eckenhoff et al. |
| 5,034,229 A | 7/1991 | Magruder et al. |
| 5,037,420 A | 8/1991 | Magruder et al. |
| 5,059,423 A | 10/1991 | Magruder et al. |
| 5,061,242 A | 10/1991 | Sampson |
| 5,110,596 A | 5/1992 | Magruder et al. |
| 5,232,702 A | 8/1993 | Pfister et al. |
| 5,246,705 A | 9/1993 | Venkatraman et al. |
| 5,279,544 A | 1/1994 | Gross et al. |
| 5,279,565 A | 1/1994 | Klein et al. |
| 5,284,133 A | 2/1994 | Burns et al. |
| 5,300,299 A | 4/1994 | Sweet et al. |
| 5,304,121 A | 4/1994 | Sahatjian |
| 5,328,696 A | 7/1994 | Noel |
| 5,348,746 A | 9/1994 | Dong et al. |
| 5,354,264 A | 10/1994 | Bae et al. |
| 5,376,378 A | 12/1994 | Li et al. |
| 5,380,760 A | 1/1995 | Wendel et al. |
| 5,431,921 A | 7/1995 | Thombre |
| 5,474,783 A | 12/1995 | Miranda et al. |
| 5,498,255 A | 3/1996 | Wong |
| 5,527,288 A | 6/1996 | Gross et al. |
| 5,546,932 A | 8/1996 | Galli |
| 5,573,668 A | 11/1996 | Grosh et al. |
| 5,587,237 A | 12/1996 | Korpman et al. |
| RE35,474 E | 3/1997 | Woodard et al. |
| 5,618,899 A | 4/1997 | Appelt et al. |
| 5,633,009 A | 5/1997 | Kenealy et al. |
| 5,645,855 A | 7/1997 | Lorenz |
| 5,656,286 A | 8/1997 | Miranda et al. |
| 5,674,192 A | 10/1997 | Sahatjian et al. |
| 5,687,748 A | 11/1997 | Conrad et al. |
| 5,714,160 A | 2/1998 | Magruder et al. |
| 5,718,700 A | 2/1998 | Edgren et al. |
| 5,779,668 A | 7/1998 | Grabenkort |
| 5,823,178 A | 10/1998 | Lloyd et al. |
| 5,891,463 A | 4/1999 | Bello et al. |
| 5,916,968 A | 6/1999 | Hariharan et al. |
| 5,939,477 A | 8/1999 | Pretzer et al. |
| 5,951,999 A | 9/1999 | Therriault et al. |
| 5,954,706 A | 9/1999 | Sahatjian |
| 5,997,501 A | 12/1999 | Gross et al. |
| 6,010,485 A | 1/2000 | Buch-Rasmussen et al. |
| 6,024,976 A | 2/2000 | Miranda et al. |
| 6,066,325 A | 5/2000 | Wallace et al. |
| RE36,754 E | 6/2000 | Noel |
| 6,152,898 A | 11/2000 | Olsen |
| 6,165,155 A | 12/2000 | Jacobsen et al. |
| 6,174,546 B1 | 1/2001 | Therriault et al. |
| 6,180,133 B1 | 1/2001 | Quan et al. |
| 6,183,434 B1 | 2/2001 | Eppstein |
| 6,193,996 B1 | 2/2001 | Effing et al. |
| 6,206,850 B1 | 3/2001 | O'Neil |
| 6,210,712 B1 | 4/2001 | Edgren et al. |
| 6,221,383 B1 | 4/2001 | Miranda et al. |
| 6,277,401 B1 | 8/2001 | Bello et al. |
| 6,293,925 B1 * | 9/2001 | Safabash et al. .............. 604/136 |
| 6,312,715 B1 | 11/2001 | Cantor et al. |
| 6,316,022 B1 | 11/2001 | Mantelle et al. |
| 6,319,245 B1 | 11/2001 | Berrigan |
| 6,334,856 B1 | 1/2002 | Allen et al. |
| 6,337,086 B1 | 1/2002 | Kanios et al. |
| 6,352,715 B1 | 3/2002 | Hwang et al. |
| 6,365,178 B1 | 4/2002 | Venkateshwaran et al. |
| 6,365,185 B1 | 4/2002 | Ritschel et al. |
| 6,368,318 B1 | 4/2002 | Visuri et al. |
| 6,387,077 B1 | 5/2002 | Klibanov et al. |
| 6,409,716 B1 | 6/2002 | Sahatjian et al. |
| 6,461,644 B1 | 10/2002 | Jackson et al. |
| 6,471,686 B1 | 10/2002 | Berrigan |
| 6,531,152 B1 | 3/2003 | Lerner et al. |
| 6,537,194 B1 | 3/2003 | Winkler |
| 6,611,707 B1 | 8/2003 | Prausnitz et al. |
| 6,623,457 B1 | 9/2003 | Rosenberg |
| 6,632,522 B1 | 10/2003 | Hyde et al. |
| 6,743,211 B1 | 6/2004 | Prausnitz et al. |
| 6,791,003 B1 | 9/2004 | Choi et al. |
| 6,796,970 B1 | 9/2004 | Klitmose et al. |
| 6,881,203 B2 | 4/2005 | Delmore et al. |
| 6,908,453 B2 | 6/2005 | Fleming et al. |
| 6,918,901 B1 * | 7/2005 | Theeuwes et al. ............ 604/500 |
| 7,097,631 B2 | 8/2006 | Trautman et al. |
| 7,226,439 B2 | 6/2007 | Prausnitz et al. |
| 7,344,499 B1 | 3/2008 | Prausnitz et al. |
| 7,678,079 B2 | 3/2010 | Shermer et al. |
| 7,713,262 B2 | 5/2010 | Adams et al. |
| 2001/0053383 A1 | 12/2001 | Miranda et al. |
| 2002/0004064 A1 | 1/2002 | Quan et al. |
| 2002/0007014 A1 | 1/2002 | Hyde et al. |
| 2002/0010412 A1 | 1/2002 | Eppstein |
| 2002/0015733 A1 | 2/2002 | Fleshner-Barak et al. |
| 2002/0099356 A1 | 7/2002 | Unger et al. |
| 2002/0106402 A1 | 8/2002 | Hartwig |
| 2002/0147208 A1 | 10/2002 | Fleshner-Barak et al. |
| 2002/0156463 A1 | 10/2002 | Berrigan |
| 2002/0183738 A1 | 12/2002 | Chee et al. |
| 2002/0193754 A1 | 12/2002 | Cho |
| 2003/0014036 A1 | 1/2003 | Varner et al. |
| 2003/0054025 A1 | 3/2003 | Cantor et al. |
| 2003/0065303 A1 | 4/2003 | Wellman et al. |
| 2003/0072792 A1 | 4/2003 | Flanigan et al. |
| 2003/0108590 A1 | 6/2003 | Peery et al. |
| 2003/0124189 A1 | 7/2003 | Zentner et al. |
| 2003/0135158 A1 | 7/2003 | Gonnelli |
| 2003/0135159 A1 * | 7/2003 | Daily et al. .................. 604/141 |
| 2003/0139495 A1 | 7/2003 | Zentner et al. |
| 2003/0143257 A1 | 7/2003 | Fleshner-Barak et al. |
| 2003/0152616 A1 | 8/2003 | Hartwig |
| 2003/0153900 A1 | 8/2003 | Aceti et al. |
| 2003/0163099 A1 | 8/2003 | Wermeling et al. |
| 2003/0187423 A1 * | 10/2003 | Wilkinson et al. ............ 604/506 |
| 2003/0216683 A1 | 11/2003 | Shekalim |
| 2003/0232198 A1 | 12/2003 | Lamberti et al. |
| 2004/0030262 A1 | 2/2004 | Fisher et al. |
| 2004/0092865 A1 | 5/2004 | Flaherty et al. |
| 2004/0102762 A1 | 5/2004 | Gilbert |
| 2004/0106893 A1 | 6/2004 | Hunter |
| 2004/0106894 A1 | 6/2004 | Hunter |
| 2004/0133159 A1 | 7/2004 | Haider et al. |
| 2004/0138603 A1 | 7/2004 | Cleary et al. |
| 2004/0142023 A1 | 7/2004 | Hartwig |
| 2004/0149288 A1 | 8/2004 | Koch |
| 2004/0176748 A1 | 9/2004 | Abramson et al. |
| 2004/0186419 A1 | 9/2004 | Cho |
| 2004/0202708 A1 | 10/2004 | Roehrig et al. |
| 2004/0204677 A1 | 10/2004 | Wellman et al. |
| 2004/0219194 A1 | 11/2004 | Finckh et al. |
| 2004/0220548 A1 | 11/2004 | Heruth et al. |
| 2005/0033230 A1 | 2/2005 | Alchas et al. |
| 2005/0038379 A1 | 2/2005 | Beebe et al. |
| 2005/0058695 A1 | 3/2005 | Anigbogu et al. |
| 2005/0137577 A1 | 6/2005 | Heruth et al. |
| 2005/0137578 A1 | 6/2005 | Heruth et al. |
| 2005/0137579 A1 | 6/2005 | Heruth et al. |
| 2005/0228340 A1 | 10/2005 | Cleary et al. |
| 2005/0261631 A1 | 11/2005 | Clarke et al. |
| 2005/0273081 A1 | 12/2005 | Olsen |
| 2005/0273082 A1 | 12/2005 | Olsen |
| 2005/0287214 A1 | 12/2005 | Ayer et al. |
| 2006/0021614 A1 | 2/2006 | Wermeling et al. |
| 2006/0078603 A1 | 4/2006 | Nguyen |
| 2006/0078604 A1 | 4/2006 | Kanios et al. |
| 2006/0084942 A1 | 4/2006 | Kim et al. |
| 2006/0094985 A1 | 5/2006 | Aceti et al. |
| 2006/0106346 A1 | 5/2006 | Sullivan et al. |
| 2006/0110596 A1 | 5/2006 | Palasz et al. |
| 2006/0135911 A1 | 6/2006 | Mittur |
| 2006/0161111 A1 | 7/2006 | Potter et al. |
| 2006/0188558 A1 | 8/2006 | Jackson et al. |

(56) References Cited

U.S. PATENT DOCUMENTS

| | | |
|---|---|---|
| 2006/0200083 A1 | 9/2006 | Freyman et al. |
| 2006/0204532 A1 | 9/2006 | John |
| 2006/0213674 A1 | 9/2006 | Dierker, Jr. et al. |
| 2006/0276744 A1 | 12/2006 | Falk |
| 2007/0021697 A1 | 1/2007 | Ginther et al. |
| 2007/0031495 A1 | 2/2007 | Eppstein et al. |
| 2007/0052139 A1 | 3/2007 | Gilbert |
| 2007/0078376 A1 | 4/2007 | Smith |
| 2007/0082038 A1 | 4/2007 | Gale et al. |
| 2007/0088267 A1 | 4/2007 | Shekalim |
| 2007/0092570 A1 | 4/2007 | Missel et al. |
| 2007/0098771 A1 | 5/2007 | Audett et al. |
| 2007/0098772 A1 | 5/2007 | Westcott et al. |
| 2007/0100355 A1 | 5/2007 | Bonde et al. |
| 2007/0104771 A1 | 5/2007 | Audett et al. |
| 2007/0134310 A1 | 6/2007 | Nedberge et al. |
| 2007/0148218 A1 | 6/2007 | Gordon |
| 2007/0161964 A1 | 7/2007 | Yuzhakov |
| 2007/0191761 A1 | 8/2007 | Boone et al. |
| 2007/0191780 A1 | 8/2007 | Modi |
| 2007/0224253 A1 | 9/2007 | Franklin |
| 2007/0260201 A1 | 11/2007 | Prausnitz et al. |
| 2007/0269522 A1 | 11/2007 | Wold |
| 2007/0293826 A1 | 12/2007 | Wall et al. |
| 2008/0009800 A1 | 1/2008 | Nickel |
| 2008/0015494 A1 | 1/2008 | Santini, Jr. et al. |
| 2008/0015522 A1 | 1/2008 | Yeshurun et al. |
| 2008/0058706 A1 | 3/2008 | Zhang et al. |
| 2008/0063698 A1 | 3/2008 | Hartwig |
| 2008/0088066 A1 | 4/2008 | Ferguson et al. |
| 2008/0091226 A1 | 4/2008 | Yeshurun et al. |
| 2008/0110463 A1 | 5/2008 | Hajgato et al. |
| 2008/0114298 A1 | 5/2008 | Cantor et al. |
| 2008/0125744 A1 | 5/2008 | Treacy |
| 2008/0152592 A1 | 6/2008 | Rebec |
| 2008/0167641 A1 | 7/2008 | Hansen et al. |
| 2008/0183144 A1 | 7/2008 | Trautman et al. |
| 2008/0208107 A1 | 8/2008 | McRae et al. |
| 2008/0214987 A1 | 9/2008 | Xu |
| 2008/0221552 A1 | 9/2008 | Leonard |
| 2008/0234656 A1 | 9/2008 | Pettis et al. |
| 2008/0312610 A1 | 12/2008 | Binks et al. |
| 2009/0007904 A1 | 1/2009 | Schuster et al. |
| 2009/0012494 A1 | 1/2009 | Yeshurun et al. |
| 2009/0028824 A1 * | 1/2009 | Chiang et al. ................ 424/85.7 |
| 2009/0041833 A1 | 2/2009 | Bettinger et al. |
| 2009/0042970 A1 | 2/2009 | Herschkowitz et al. |
| 2009/0043279 A1 | 2/2009 | Kaspar et al. |
| 2009/0048555 A1 | 2/2009 | Stryker et al. |
| 2009/0060986 A1 | 3/2009 | Yum et al. |
| 2009/0099545 A1 | 4/2009 | Nilsson et al. |
| 2009/0118662 A1 | 5/2009 | Schnall |
| 2009/0221971 A1 | 9/2009 | Mejlhede et al. |
| 2010/0030156 A1 | 2/2010 | Beebe et al. |
| 2010/0030198 A1 | 2/2010 | Beebe et al. |
| 2010/0049128 A1 | 2/2010 | McKenzie et al. |
| 2010/0330589 A1 * | 12/2010 | Bahrami et al. ................ 435/7.9 |
| 2011/0172609 A1 | 7/2011 | Moga et al. |
| 2011/0172637 A1 | 7/2011 | Moga et al. |
| 2011/0172638 A1 * | 7/2011 | Moga et al. .................. 604/506 |
| 2011/0172639 A1 * | 7/2011 | Moga et al. .................. 604/506 |
| 2011/0172645 A1 | 7/2011 | Moga et al. |
| 2012/0123387 A1 * | 5/2012 | Gonzalez et al. ............. 604/506 |

OTHER PUBLICATIONS

Roxhed, Niclas, A Fully Integrated Microneedle-based Transdermal Drug Delivery System, Royal Institute of Technology, Stockholm, Sweden, 2007, 93 pgs.

* cited by examiner

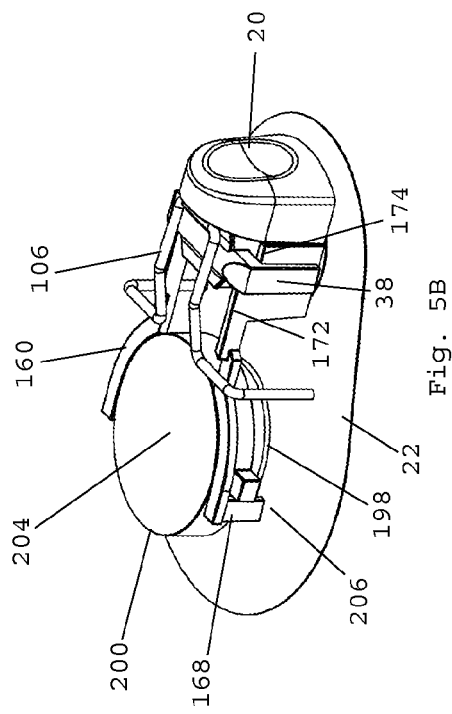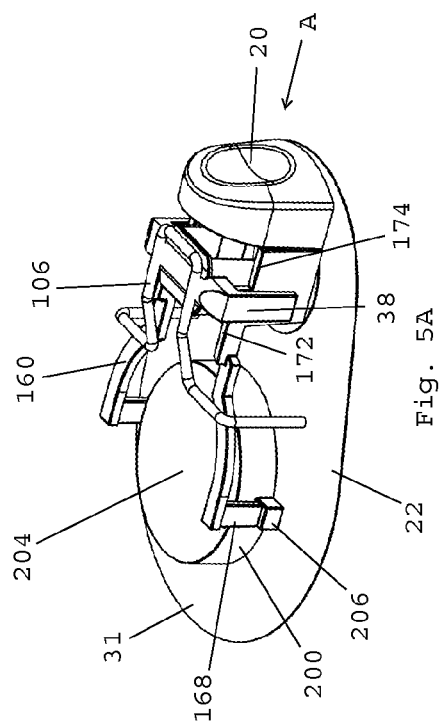

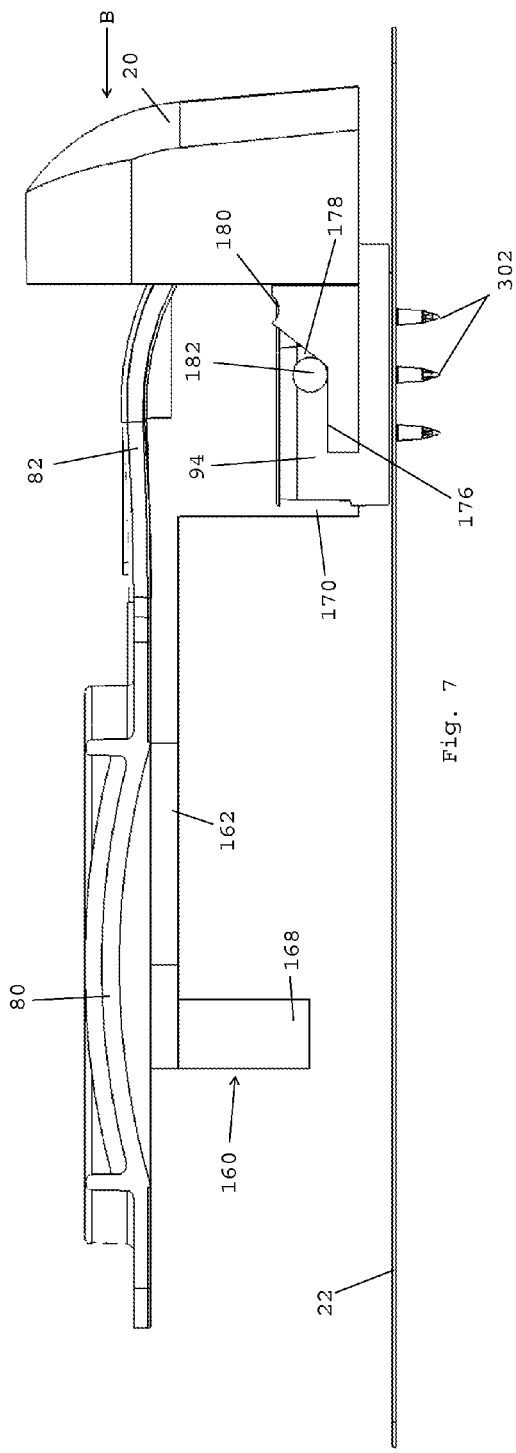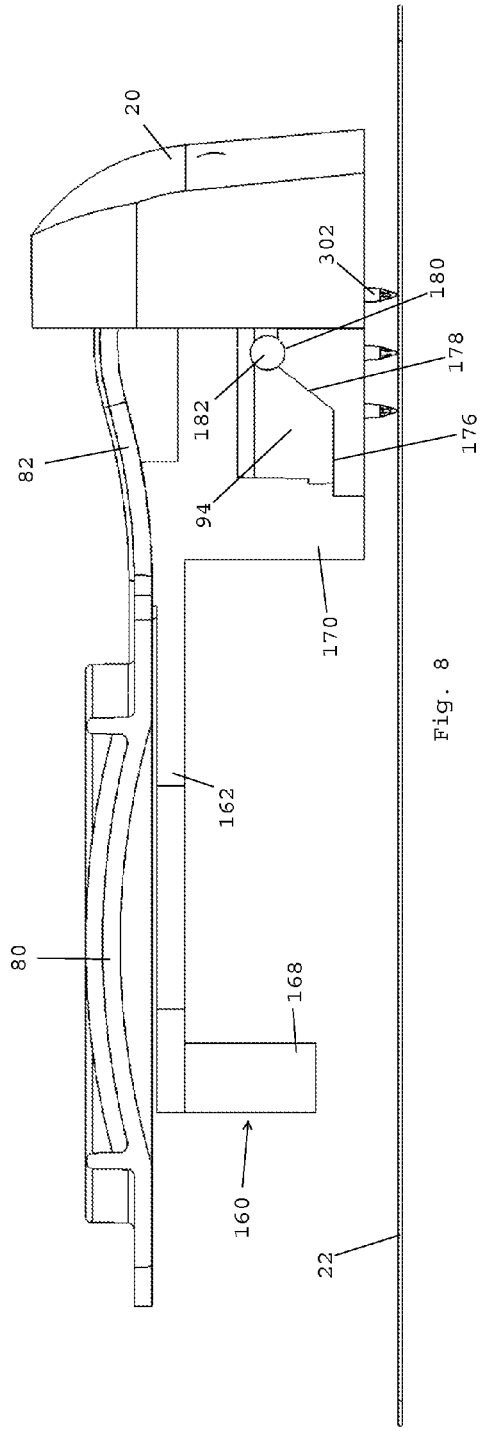

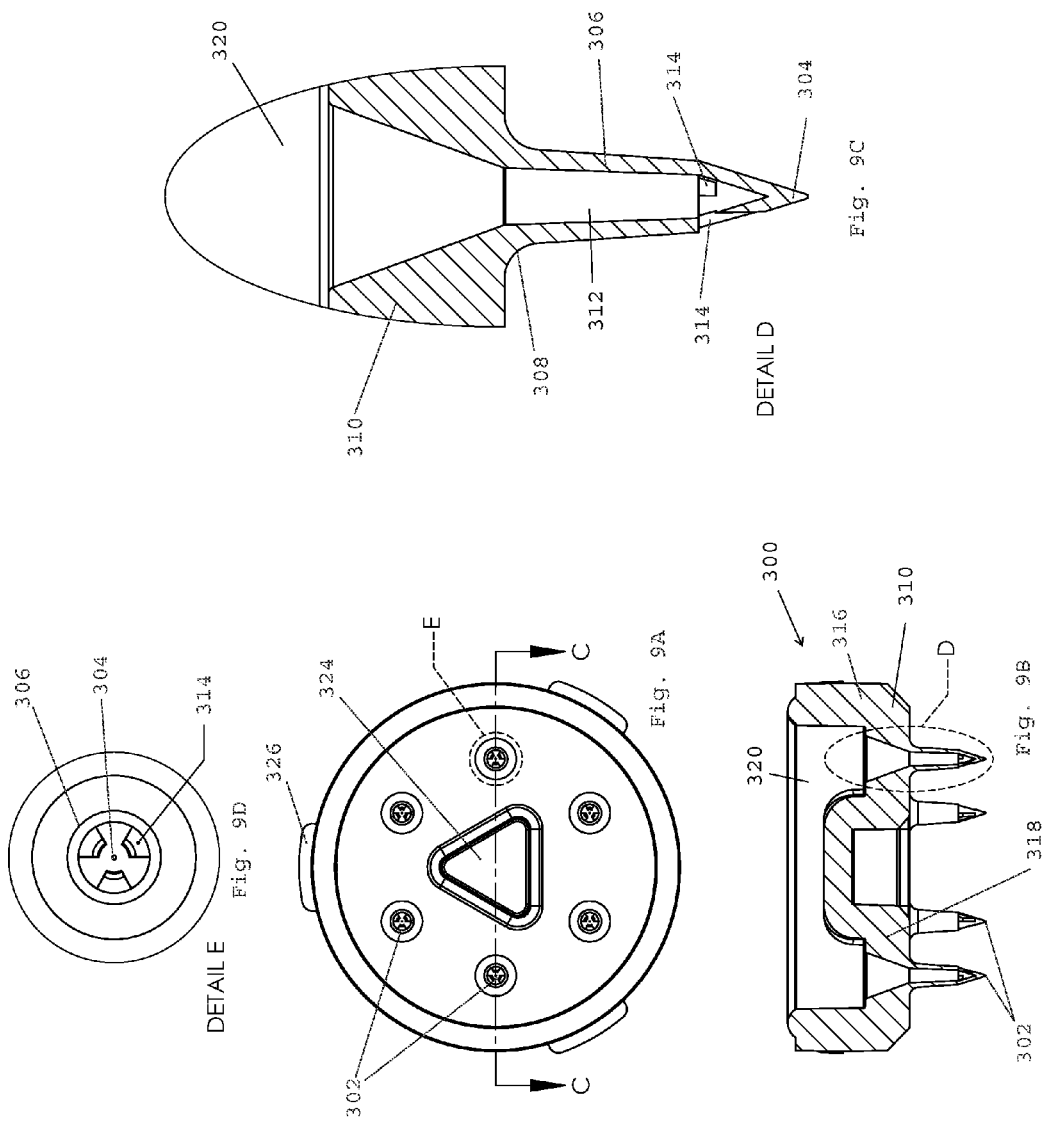

WEARABLE DRUG DELIVERY DEVICE HAVING SPRING DRIVE AND SLIDING ACTUATION MECHANISM

CROSS-REFERENCE TO RELATED PATENT APPLICATIONS

This patent application claims the benefit of U.S. Provisional Patent Application No. 61/409,824, filed Nov. 3, 2010. This application is also related to U.S. patent application Ser. Nos. 12/684,823, 12/684,832, 12/684,834, 12/684,840, and 12/684,844, each of which are hereby incorporated by reference in their entirety.

FIELD OF THE INVENTION

The present invention relates generally to the field of drug delivery devices. The present invention relates specifically to wearable active transdermal drug delivery devices including which facilitate drug delivery using one or more microneedles as the point of drug delivery.

BACKGROUND OF THE INVENTION

An active agent or drug (e.g., pharmaceuticals, vaccines, hormones, nutrients, etc.) may be administered to a patient through various means. For example, a drug may be ingested, inhaled, injected, delivered intravenously, etc. In some applications, a drug may be administered transdermally. In some transdermal applications, such as transdermal nicotine or birth control patches, a drug is absorbed through the skin. Passive transdermal patches often include an absorbent layer or membrane that is placed on the outer layer of the skin. The membrane typically contains a dose of a drug that is allowed to be absorbed through the skin to deliver the substance to the patient. Typically, only drugs that are readily absorbed through the outer layer of the skin may be delivered with such devices.

Other drug delivery devices are configured to provide for increased skin permeability to the delivered drugs. For example, some devices use a structure, such as one or more microneedles, to facilitate transfer of the drug into the skin. Solid microneedles may be coated with a dry drug substance. The puncture of the skin by the solid microneedles increases permeability of the skin allowing for absorption of the drug substance. Hollow microneedles may be used to provide a fluid channel for drug delivery below the outer layer of the skin.

The invention provides such a drug delivery device. These and other advantages of the invention, as well as additional inventive features, will be apparent from the description of the invention provided herein.

BRIEF SUMMARY OF THE INVENTION

One embodiment of the invention is a device for delivering a drug to the skin of a subject that includes a base portion for resting on the skin surface, a drug reservoir supported by the base portion, and at least one hollow microneedle with a tip portion for penetrating the skin surface. The hollow microneedle is in fluid communication with the reservoir. A first stored energy mechanism releasable to force the tips into the skin, a second stored energy mechanism releasable to force drug from the reservoir through the needle, and a trigger moveably supported by the base portion and coupled to the first and second stored energy mechanisms to release the mechanisms such that the tip is forced into the skin before the drug is forced through the needle.

Another embodiment of the invention is a microneedle array that includes a plurality of hollow microneedles each having one or more side ports, a lumen, and a solid tip. The microneedle array has a bottom plane with a center axis parallel to the microneedles and side walls. The bottom plane and side walls define an internal cavity with a depth greater than height of the microneedles, so that one microneedle array may be contacted with a second microneedle array without contacting the microneedles of the first microneedle array with the bottom plane of the second microneedle array when the microneedle arrays are coaxially aligned along their center axes.

In another embodiment of the invention is a device for delivering a drug to the skin of a subject that includes a base portion defining a bottom for resting on the skin surface, a drug reservoir supported by the base portion, and at least one hollow microneedle having a tip portion for penetrating the skin of the subject. The microneedles are in fluid communication with the reservoir. A first stored energy mechanism is releasable to force the tips into the skin, and a second stored energy mechanism releasable to force drug from the reservoir through the needles. A trigger is moveably supported by the base portion and coupled to the first and second stored energy mechanisms, to release the mechanisms so that the tip is forced from a position above the to a position below the bottom plane before the drug is forced through the needle.

BRIEF DESCRIPTION OF THE DRAWINGS

FIG. 5A is a perspective view of internal components of a drug delivery device in an pre-activation position;

FIG. 5B is a perspective view of internal components of a drug delivery device in an activated position;

FIG. 7 is a side view of a trigger assembly and drug reservoir in an activated position;

FIG. 8 is a side view of a trigger assembly and a drug reservoir in a needle retraction position;

FIG. 9A is a bottom view of a microneedle array;

FIG. 9B is a side cross-sectional view of a microneedle array along line C-C;

FIG. 9C is a side cross-sectional detail view of an individual microneedle taken from oval D;

FIG. 9D is a bottom detail view of a microneedle taken from circle E;

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION

Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Drug Delivery Device

Referring generally to FIGS. 1-10, a drug delivery device is shown according to an exemplary embodiment. The drug delivery device is placed in contact with the skin of a subject (e.g., a human or animal, etc.) prior to delivery of the substance to the subject. After the device is affixed to the skin of the subject, the device is activated in order to deliver the substance to the subject. Following delivery of the substance, the device is removed from the skin. During storage and transport, the drug delivery device may also be enclosed in an exterior package to protect the device and ensure sterility.

The delivery device described herein may be utilized to deliver any substance that may be desired. In one embodiment, the substance to be delivered is a drug, and the delivery device is a drug delivery device configured to deliver the drug to a subject. As used herein the term "drug" is intended to include any substance delivered to a subject for any therapeutic, preventative, or medicinal purpose (e.g., vaccines, pharmaceuticals, nutrients, nutraceuticals, etc.). In one such embodiment, the drug delivery device is a vaccine delivery device configured to deliver a dose of vaccine to a subject. In one embodiment, the delivery device is configured to deliver a flu vaccine. The embodiments discussed herein relate primarily to a device configured to deliver a substance intradermally. In other embodiments, the device may be configured to deliver a substance transdermally or may be configured to deliver drugs directly to an organ other than the skin.

Figure 1:
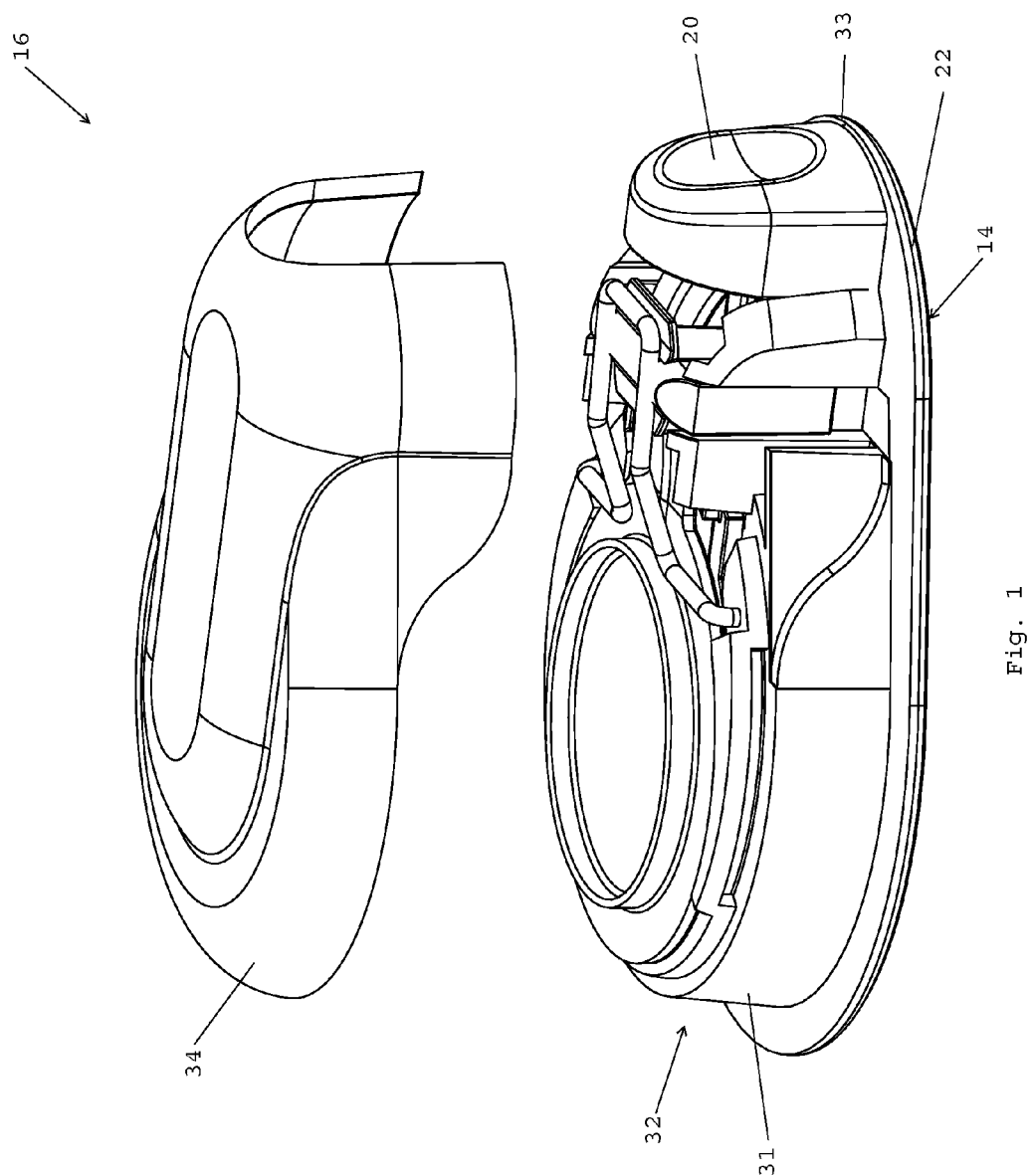
FIG. 1 is a perspective view of a drug delivery device having a cover according to an exemplary embodiment, shown with the cover removed.

Referring to FIG. 1, a drug delivery device 16 is shown including a base portion 32 and cover 34, shown with cover 34 lifted vertically from base portion 32. A rear direction 31 and a front direction 33 are shown on base portion 32. Base portion 32 may be provided with an attachment element shown as, but not limited to, an adhesive layer 22. Additionally, adhesive layer 22 may be covered with a protective barrier or film 14. Drug delivery device 16 is shown with a button 20 located at the front 33 of base portion 32.

Figure 3B:
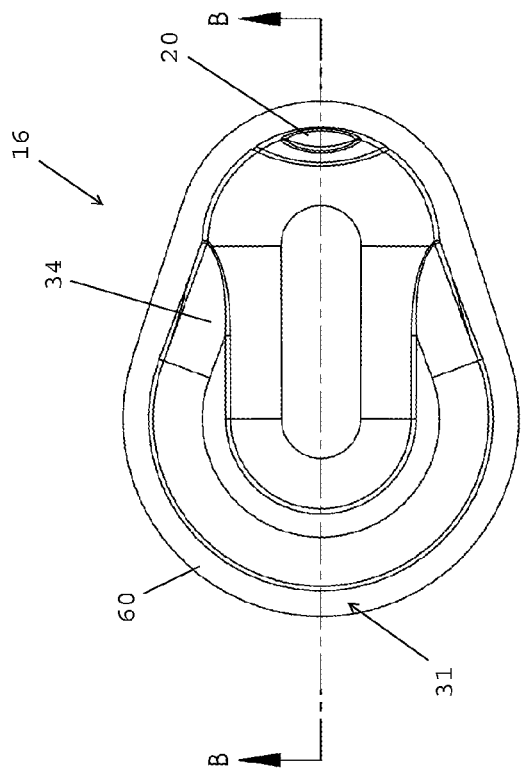
FIG. 3B is a top view of a drug delivery device in an activated position.
Figure 3A:
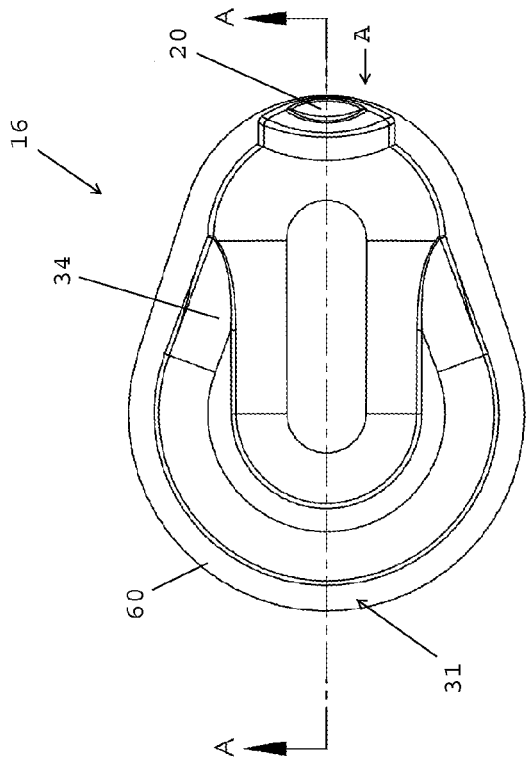
FIG. 3A is a top view of a drug delivery device in an pre-activation position.

To use delivery device 16 to deliver a drug to a subject, protective barrier 14 is removed exposing adhesive layer 22. Protective barrier 14 may include a tab that facilitates gripping of protective barrier 14 during removal. Once adhesive layer 22 is exposed, delivery device 16 is placed on the skin. Adhesive layer 22 is made from an adhesive material that forms a nonpermanent bond with the skin of sufficient strength to hold delivery device 16 in place on the skin of the subject during use. With delivery device 16 adhered to the skin of the subject, button 20 is pressed to trigger delivery of the drug to the patient. In a preferred embodiment, a patient or user can exert a squeezing motion between button 20 and rear 31 using the thumb and one or more fingers. FIG. 3A shows drug delivery device 16 in an assembled, pre-activation condition, and FIG. 3B shows the same device when the device is placed in an activated condition. As shown in FIGS. 3A, 3B, 5A, and 5B, pressing button 20 translates trigger element 160 towards the rear 31 of the drug delivery device, in the direction shown by arrow A and substantially parallel to the skin of the patient, thereby minimizing any shear force exerted on drug delivery device 16 with respect to the skin. Additionally, exertion of activation force in a direction substantially parallel to the skin of the subject may also minimize distortion of the skin due to pressing an activation button, thereby improving the seating of microneedles 302 (discussed in further detail below) into the skin of the subject. When delivery of the drug is complete, delivery device 16 may be detached from the skin of the subject by applying sufficient force to overcome the grip generated by adhesive layer 22.

In one embodiment, delivery device 16 is sized to be conveniently wearable by the user during drug delivery. In one embodiment, the length of delivery device 16 along the device's long axis is 53.3 mm, the length of delivery device 16 along the device's short axis (at its widest dimension) is 40.8 mm, and the height of delivery device 16 is 14.7 mm. However, in other embodiments other dimensions are suitable for a wearable drug delivery device. For example, in another embodiment, the length of delivery device 16 along the device's long axis is between 40 mm and 80 mm, the length of delivery device 16 along the device's short axis (at its widest dimension) is between 30 mm and 60 mm, and the height of delivery device 16 at button 20 following activation is between 5 mm and 30 mm. In another embodiment, the length of delivery device 16 along the device's long axis is between 50 mm and 55 mm, the length of delivery device 16 along the device's short axis (at its widest dimension) is between 45 mm and 50 mm, and the height of delivery device 16 is between 10 mm and 20 mm.

While in the embodiments shown the attachment element is shown as adhesive layer 22, other attachment elements may be used. For example, in one embodiment, delivery device 16 may be attached via an elastic strap. In another embodiment, delivery device 16 may not include an attachment element and may be manually held in place during delivery of the drug.

Figure 2:
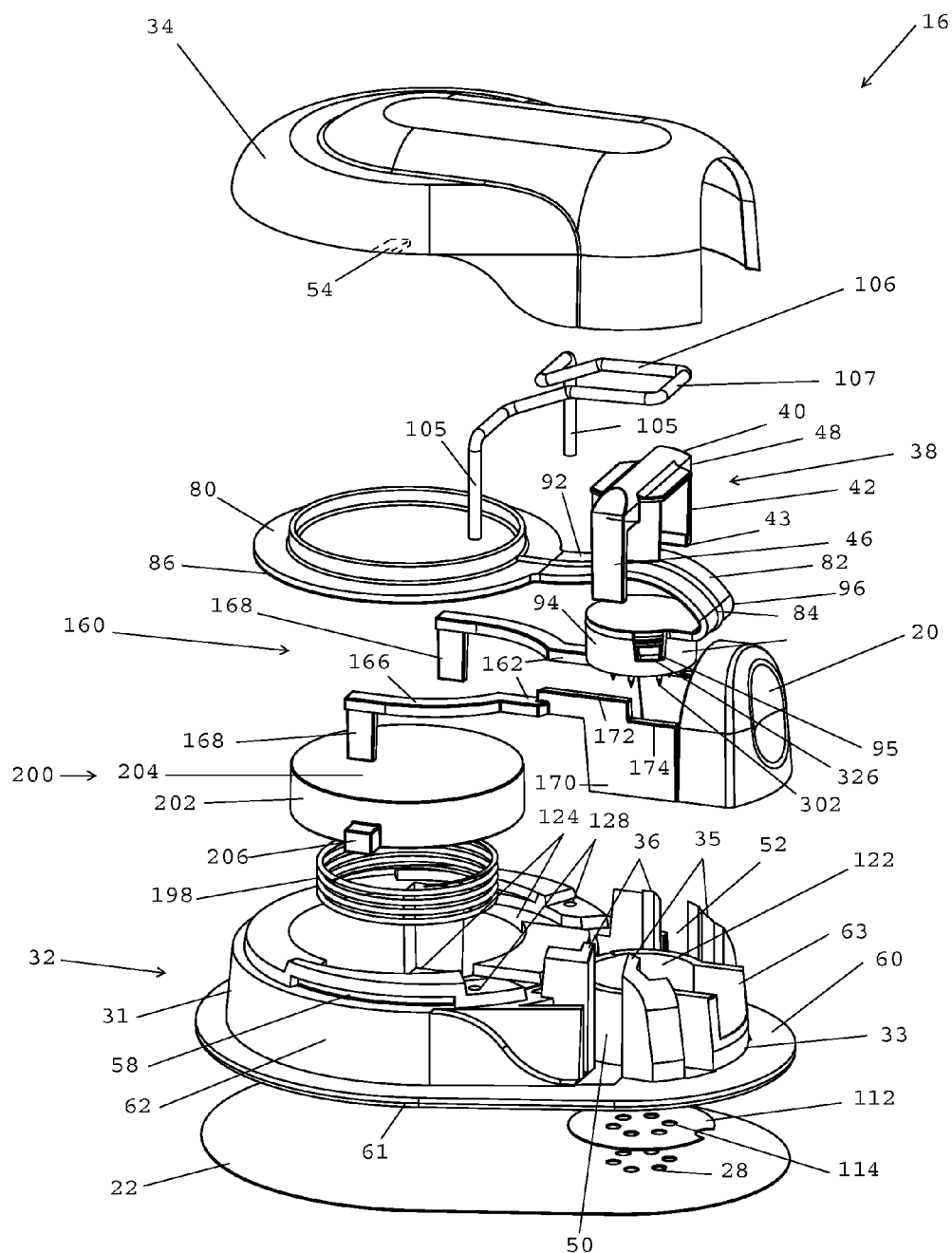
FIG. 2 is an exploded perspective view of a drug delivery device according to an exemplary embodiment.

Referring to FIG. 2, an exploded perspective view of delivery device 16 is shown. Base portion 32 includes a flange 60, a bottom tensile member, shown as bottom wall 61, a first support portion 62, and a second support portion 63. In the embodiment shown, bottom wall 61 is a rigid wall that is positioned below flange 60. Bottom wall 61 may be provided with an opening to receive needle screen 112. Needle screen 112 includes one or more holes 114 that are sized and positioned to align with needle holes 28 in adhesive layer 22. In this manner, holes 114 in needle screen 112 and holes 28 in adhesive layer 22 form channels for the passage of microneedles 302 through bottom wall 61 when the device is placed in an activated configuration. In another embodiment, needle holes 114 may be formed directly into bottom wall 61.

As shown in FIG. 2, the outer surface of first support portion 62 is generally cylindrically shaped and extends upward from flange 60. First support portion 62 defines a cylindrical opening or cavity to receive coiled compression spring 198 and piston 200. Piston 200 is shown as including a generally cylindrical side wall 202 and a convex piston top surface 204. Piston 200 further includes at least one piston tab 206. In a preferred embodiment, piston 200 is provided with piston tab 206 and a second piston tab placed on the opposite side of piston 200. First support portion 62 also includes a pair of cylindrical channels 128 that receive the downwardly extending segments 105 of needle spring 106. First support portion 62 is further provided with horizontal support surfaces 124 which slidably support trigger arms 162 of trigger element 160.

In a preferred embodiment, cover 34 is ultrasonically welded to base portion 32. In another embodiment, base portion 32 include may a recess 58 and second recess similar to recess 58 on the opposite side of base portion 32. Both recess 58 and the opposing recess are formed in the upper peripheral edge of the outer surface of first support portion 62. Top cover 34 includes a tab 54 and second tab similar to tab 54 on the opposite side of top cover 34 that each extend inwardly from a portion of the inner edge of cover 34. When top cover 34 is mounted to base portion 32, tab 54 is received within recess 58 is and the similar tab is received within the similar recess on the opposing side of base portion 32, thereby holding top cover 34 to base portion 32. In other embodiments, cover 34 may be attached to base portion 32 with an adhesive or with one or more screws.

Still referring to FIG. 2, second support portion 63 is generally cylindrically shaped and extends upward from flange 60. Second support portion 63 includes front posts 35 and rear posts 36 defining a first channel 50 and a second channel 52.

Second support portion 63 also includes a central cavity 122 sized to slidably receive shuttle 38. Shuttle 38 is provided with first guide arm 46 and second guide arm 48. Guide arms 46 and 48 are slidably received within channels 50 and 52 respectively, when shuttle 38 is received in the center cavity 122 of second support portion 63. Channels 50 and 52 act as a vertical movement guide for guide arms 46 and 48 respectively, to help ensure that shuttle 38 moves a generally linearly downward direction during activation of delivery device 16.

Drug delivery device 16 also includes a microneedle activation element or microneedle actuator, shown as, but not limited to, needle spring 106. As explained in greater detail below, needle spring 106 stores energy, which upon activation of drug delivery device 16, is transferred to one or more microneedles causing the microneedles to penetrate the skin. In other embodiments, other spring types, such as a coiled compression spring or leaf spring may instead be employed.

Shuttle 38 further includes a top wall 40 having a generally hemi-cylindrical top surface providing points of contact between top wall 40 and U-shaped portion 107 of needle spring 106. As needle spring 106 propels shuttle 38 downwards towards bottom wall 61, needle spring 106 rotates slightly about top wall 40, maintaining contact between U-shaped contact portion 107 and top wall 40. Shuttle 38 is also includes a generally cylindrically shaped shuttle wall or skirt 42. Skirt 42 is slidably received by central cavity 122. The bottom edge 43 of skirt 42 contacts the top surface of cup portion 94, described in further detail below.

Trigger element 160 includes button 20, and a pair of trigger arms 162. In a preferred embodiment, trigger arms include curved portion 166 and a generally planar trigger side walls 170. The top edges of trigger side walls 170 include shuttle support rails 172 and shuttle release notch 174. Trigger arms 162 are further provided with trigger fingers 168. Trigger element 160 is slidably received by base portion 32 such that trigger arms 162 rest atop horizontal support surfaces 124 of first support portion 62. Trigger element 160 is thereby permitted to move towards rear 31 of base portion 32 when button 20 is pressed.

Figure 6:
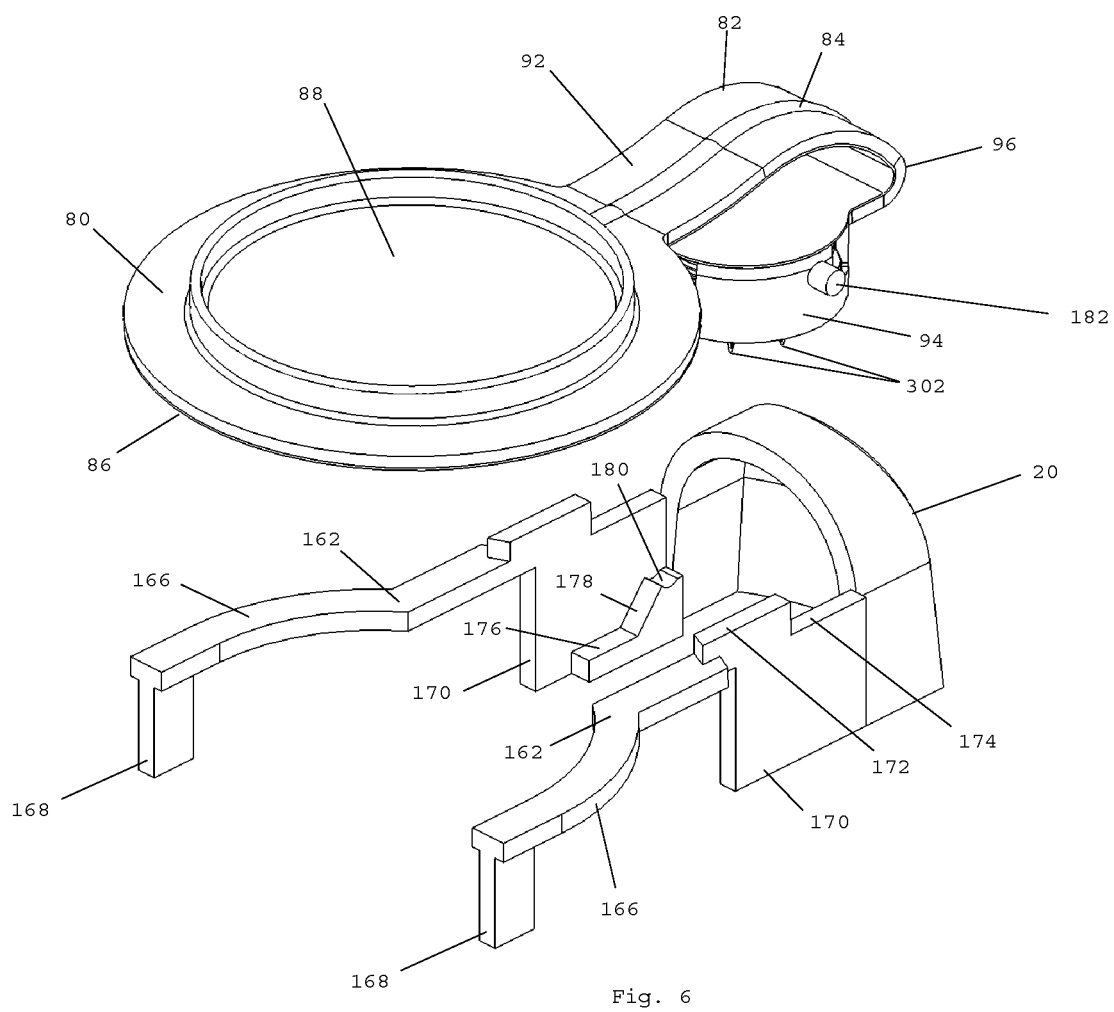
FIG. 6 is an exploded perspective view of a trigger assembly and drug reservoir showing needle retraction features.

Still referring to FIG. 2, drug delivery device 16 further includes a drug reservoir base 80 and drug channel arm 82. The lower surface of drug channel arm 82 includes a depression or groove 84 that extends from reservoir base 80 along the length of drug channel arm 82. As shown in FIG. 2 and FIG. 6, groove 84 appears as a rib protruding from the upper surface of drug channel arm 82. Drug delivery device 16 further includes a flexible barrier film 86 adhered to the inner surfaces of both drug reservoir base 80 and drug channel arm 82. Barrier film 86 is adhered to form a fluid tight seal or a hermetic seal with drug reservoir base 80 and channel arm 82. In this arrangement (shown best in FIGS. 4A and 4B), the inner surface of drug reservoir base 80 and the inner surface of barrier film 86 form a drug reservoir 88, and the inner surface of groove 84 and the inner surface of barrier film 86 form a fluid channel, shown as, but not limited to, drug channel 90. In this embodiment, drug channel arm 82 acts as a conduit to allow fluid to flow from drug reservoir 88. As shown, drug channel arm 82 includes a first portion 92 extending from drug reservoir base 80, a microneedle attachment portion, shown as, but not limited to, cup portion 94, and a generally U-shaped portion 96 joining the first portion 92 to the cup portion 94. As shown, needle cup 94 receives a microneedle array 300, described in further detail below. Needle cup 94 may be further provided with openings 95 configured to receive an installation tab 326 of a microneedle array. In the embodiment shown, drug reservoir base 80 and drug channel arm 82 are made from an integral piece of polypropylene. However, in other embodiments, drug reservoir base 80 and drug channel arm 82 may be separate pieces joined together and may be made from other plastics or other materials.

Referring to FIGS. 4 and 5, drug delivery device 16 includes a reservoir actuator or force generating element, shown as, but not limited to, piston spring 198, and a force distribution element, shown as, but not limited to, piston 200. Piston spring 198 is shown as a coiled compression spring. In other embodiments, other types of springs may be used, such as a torsion spring or a leaf spring. Piston spring 198 is positioned inside piston 200 to provide an upward motivating force against piston 200 when drug delivery device 16 is placed in an activated condition. Prior to activation, trigger fingers 168 are in vertical contact with piston tabs 206, thereby preventing piston spring 198 from translating piston 200 upwards.

Figure 4A:
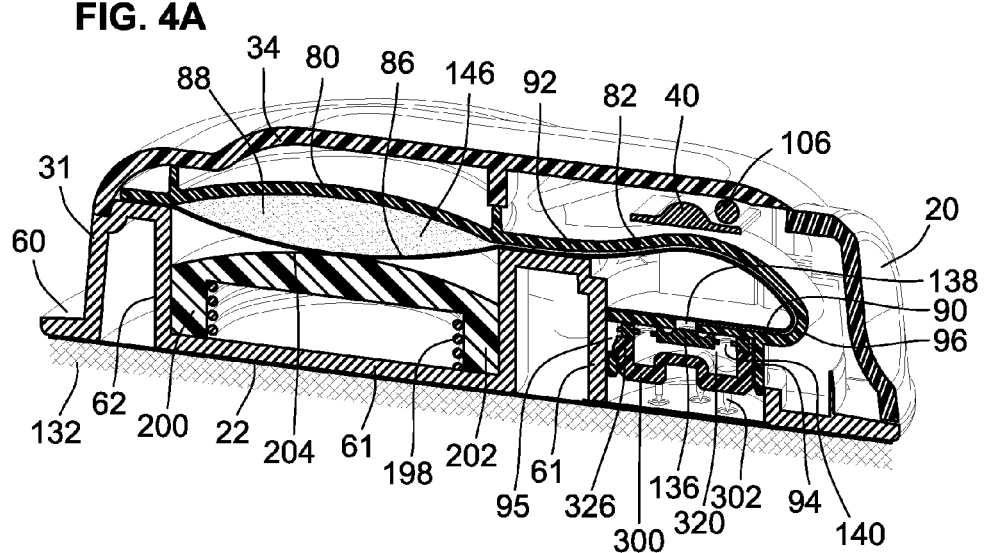
FIG. 4A is an isometric sectional view along line A-A of FIG. 3A of a drug delivery device in an pre-activation position.

Referring to FIG. 4A, an isometric sectional view of delivery device 16 is shown attached or adhered to skin 132 of a subject prior to activation of the device. As shown, adhesive layer 22 provides for gross attachment of the device to skin 132 of the subject. Delivery device 16 includes a microneedle component, shown as, but not limited to, microneedle array 300, having a plurality of microneedles, shown as, but not limited to, hollow microneedles 302, extending from the lower surface of microneedle array 300. In the embodiment shown, microneedle array 300 includes an internal channel 320 allowing fluid communication from the upper surface of microneedle array 300 to the tips or ports of hollow microneedles 302, shown in further detail below.

Delivery device 16 also includes a valve component, shown as, but not limited to, check valve 136. Both microneedle array 300 and check valve 136 are mounted within cup portion 94. Drug channel 90 terminates in an aperture or hole 138 positioned above check valve 136. In the pre-activation or inactive position shown in FIG. 4A, check valve 136 blocks aperture 138 at the end of drug channel 90 preventing a substance, shown as, but not limited to, drug 146, within drug reservoir 88 from flowing into microneedle array 300. While the embodiments discussed herein relate to a drug delivery device that utilizes hollow microneedles, in other various embodiments, other microneedles, such as solid microneedles, may be utilized.

Referring to FIGS. 4 and 5, during activation trigger fingers 168 are displaced in the direction shown by arrow A towards the rear 31 of base portion 32, thereby allowing piston 200 to move in an upward direction. As piston spring 198 uncompresses, piston 200 is moved upward and forces barrier film 86 upward toward drug reservoir base 80. As barrier film 86 is pushed upward by piston 200, pressure within drug reservoir 88 and drug channel 90 increases. When the fluid pressure within drug reservoir 88 and drug channel 90 reaches a threshold, check valve 136 is forced open allowing drug 146 within drug reservoir 88 to flow through aperture 138 at the end of drug channel 90. As shown, check valve 136 includes a plurality of holes 140, and microneedle array 300 includes a plurality of hollow microneedles 302. Drug channel 90, aperture 138, plurality of holes 140 of check valve 136, internal channel 320 of microneedle array 300 and hollow microneedles 302 define a fluid channel between drug reservoir 88 and the subject when check valve 136 is opened. Thus, drug 146 is delivered from reservoir 88 through drug channel 90 and out of hollow microneedles 302 to the skin of the subject by the pressure generated by piston spring 198.

Figure 4B:
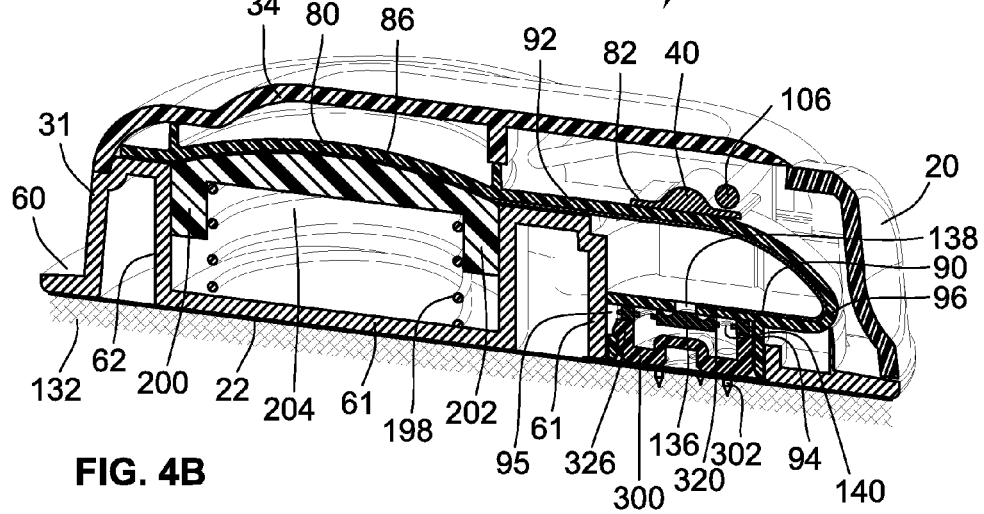
FIG. 4B is an isometric sectional view along line B-B of FIG. 3B of a drug delivery device in an activated position.

As shown in FIG. 4B, activation of the device causes piston spring 198 and piston 200 to exert a pressure on drug reservoir 88, thereby causing a fluid pressure in drug channel 90. In the embodiment shown, check valve 136 is a segment of flexible material (e.g., medical grade silicon) that flexes away from aperture 138 when the fluid pressure within drug channel 90 reaches a threshold, thereby placing drug channel 90 in fluid communication with hollow microneedles 302. In one embodiment, the pressure threshold needed to open check valve 136 is about 0.5-1.0 pounds per squire inch (psi). In various other embodiments, check valve 136 may be a rupture valve, a swing check valve, a ball check valve, or other type of valve the allows fluid to flow in one direction. In the embodiment shown, needle spring 106 is shown as a torsion spring that stores energy for activation of the microneedle array until the activation control, shown as button 20, is pressed. In other embodiments, other energy storage or force generating components may be used to activate the microneedle component.

In one embodiment, delivery device 16 and reservoir 88 are sized to deliver a dose of drug of up to approximately 500 microliters. In other embodiments, delivery device 16 and reservoir 88 are sized to allow delivery of other volumes of drug (e.g., up to 200 microliters, up to 400 microliters, up to 1 milliliter, etc.).

FIGS. 5A and 5B illustrate the operation of trigger element 160, needle spring 106, shuttle 38, and piston 200. As shown in FIG. 5A, in the pre-activation position shuttle 38 is supported by shuttle support rails 172. U-shaped contact portion 107 of needle spring 106 bears against top contact cylinder 40 of shuttle 38, and exerts a downward force on shuttle 38. Prior to activation trigger fingers 168 also bear against piston tabs 206, thereby constraining piston 200 from moving in an upward direction in response to the force exerted by piston spring 198. Piston spring 198 is installed in a first compressed state, thereby storing energy.

As shown in FIG. 5B, when button 20 is pressed, trigger element 160 is horizontally translated towards the rear 31 of base portion 32 and parallel to bottom wall 61 and the skin of a subject, in a sliding motion. As trigger element 160 slides towards the rear 31 of base 32, trigger fingers 168 slide off piston tabs 206. Additionally, the sliding movement of trigger element 160 positions shuttle release notches 174 directly below shuttle 38. Needle spring 106 thereby forces shuttle 38, needle cup 94, and microneedle array 300 downwards and inserts microneedles 302 into the skin of the subject. As also shown in FIG. 5B, removal of trigger fingers 168 from contact with piston tabs 206 allows piston 200 to move upwards in response to the force provided by piston spring 198. In the embodiment shown, trigger element 160 releases piston 200 and shuttle 38 at substantially the same time. In other embodiments, the position of piston tabs 206, the width of trigger fingers 168, and/or the width of shuttle release notches 174 may be varied such that piston 200 is released before or after shuttle 38 is placed in its activated position.

In one embodiment, first support 62 may be provided with a window or cutout allowing observation of the upward movement of piston 200, or of piston tab 206, thereby providing a visual indicator showing the progress of drug delivery. Accordingly, a subject or user can observe that piston 200 has ceased movement and that drug delivery has therefore been completed, indicating that drug delivery device 16 may be removed from the skin of the subject without premature loss of the drug to be delivered.

Referring to FIGS. 6, 7, and 8, an embodiment including a needle retraction feature is shown. After device 16 is placed in an active position and drug 146 is delivered to the skin of the subject, the device may be placed in a retracted or "safe" position. As shown in FIG. 6, the inside of trigger side walls 170 may be provided with a ramp structure including a delivery ramp surface 176, a sloped ramp portion 178, and a detent cup 180. In a preferred embodiment, the inside of each trigger side wall 170 is provided with a ramp structure. In another embodiment, only one trigger side wall 170 may be provided with a ramp structure. Needle cup 94 is also provided with a pair of generally cylindrical retraction tabs 182 positioned on opposite sides of cup 94.

FIGS. 7 and 8 show the positions of trigger element 160 and needle cup 94 relative to adhesive layer 22 during needle retraction. As shown in FIG. 7, when the device is placed in an activated configuration and during drug delivery, retraction tabs 182 rest atop delivery ramp surface 176. Microneedles 302 extend below the bottom plane of drug delivery device, shown here as adhesive layer 22, thereby permitting drug delivery through microneedles 302. Following completion of drug delivery, button 20 is pressed in the direction of arrow B. As shown in FIG. 8, trigger element 160 is moved further towards the rear 31 of drug delivery device 16, thereby urging retraction tabs 182 upward along sloped ramp portion 178 and into detent cup 180. The upward motion of retraction tabs 182 retracts needle cup 94 and microneedles 302 into the base portion of the drug delivery device, above the plane of adhesive layer 22, thereby preventing further contact with the microneedles and allowing for safe disposal.

Referring generally to FIGS. 11-14, a drug delivery device 400 is shown according to another exemplary embodiment, where like numbers refer to like features. As with the first exemplary embodiment shown as drug delivery device 16, drug delivery device 400 is placed in contact with the skin of a subject, activated to deliver a substance to the subject, and removed from the subject after delivery is complete.

Figure 11:
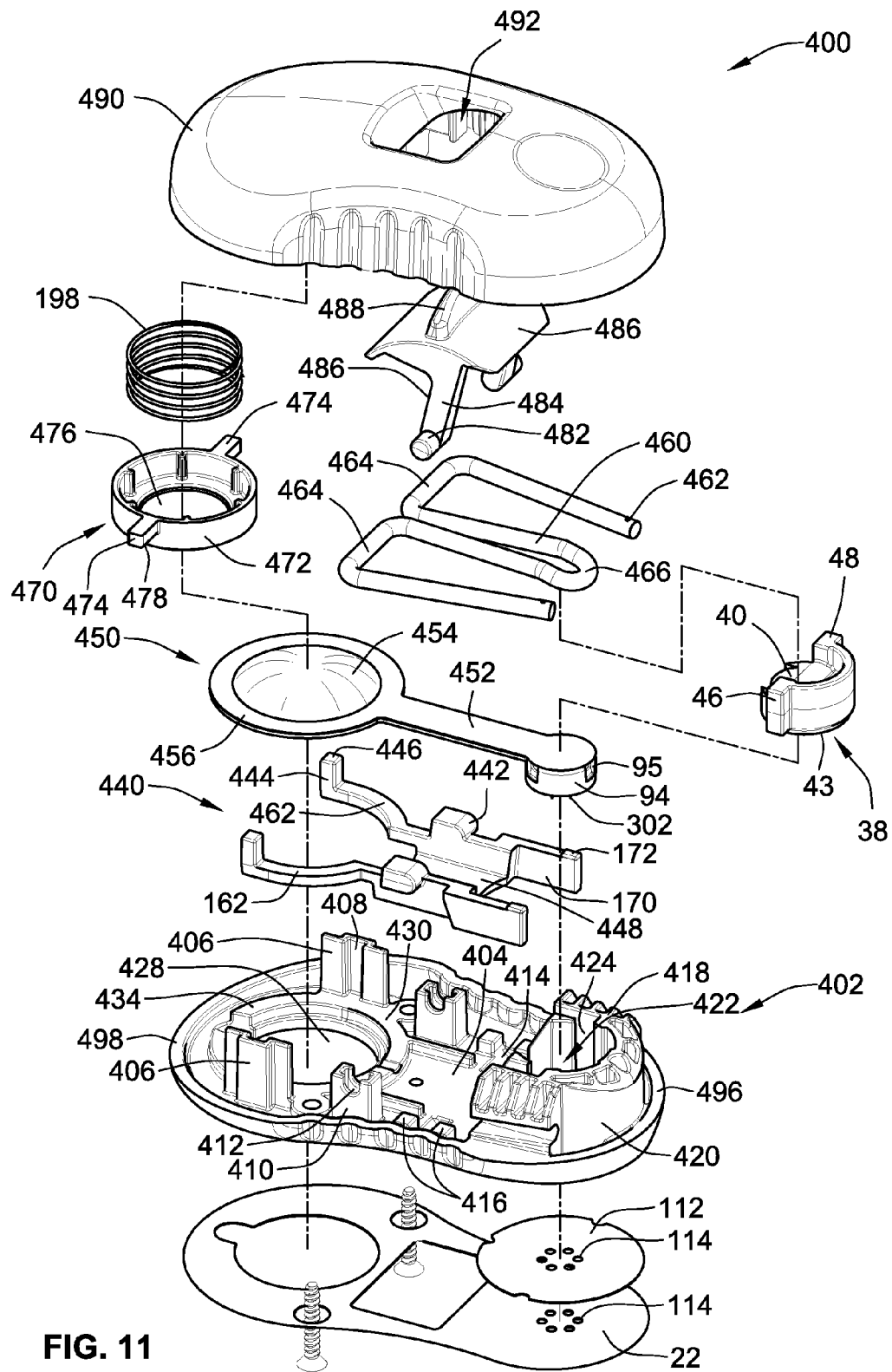
FIG. 11 is an exploded perspective view of a drug delivery device according to a second exemplary embodiment.
Figure 12A:
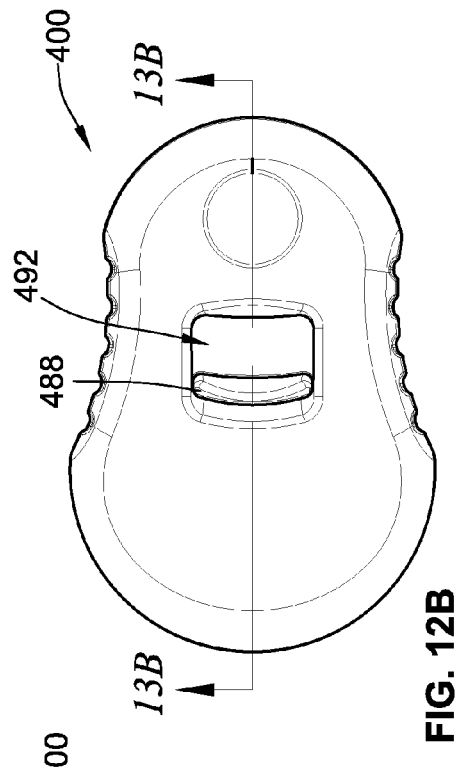
FIG. 12A is a top view of the second exemplary drug delivery device in an pre-activation position.
Figure 12B:
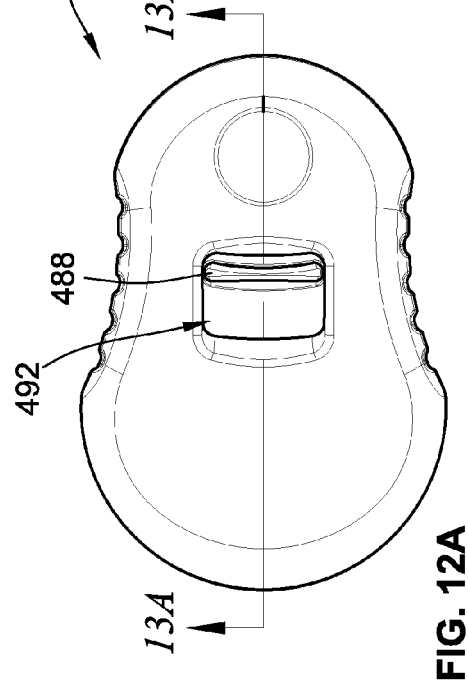
FIG. 12B is a top view of the second exemplary drug delivery device in an activated position.

Referring to FIG. 11, an exploded perspective view of delivery device 400 is shown. Base portion 402 includes a bottom tensile member, shown as bottom wall 404. Bottom wall 404 is generally planar and is further provided with piston guide portions 406, spring support portions 410, lever fulcrums 414, and a shuttle support portion 418. As shown, bottom wall 404 of base portion 402 is provided with an annular opening 428. In other embodiments, bottom wall 404 of base portion 402 is not provided with an annular opening 428. In the embodiment shown, base portion 402 is molded as a single piece. In other embodiments, base portion 402 may be molded from separate pieces and joined or assembled as is generally known in the art. In a preferred embodiment, base portion 402 is molded from a plastic.

In the embodiment shown in FIG. 11, cover 490 is mechanically fastened to base portion 402. In other embodiments, cover 490 may be attached to base portion 402 with an adhesive or by ultrasonic welding. Cover 490 is provided with an annular opening 492, thereby permitting operation of activation lever 480.

Base portion 402 also includes a support surface 430. Support surface 430 of base portion 402 is generally planar and parallel to bottom wall 404 of base portion 402. As shown, support surface 430 is a continuous, planar surface including a circular portion 432 surrounding annular opening 428, and guide rails 434. In other embodiments, support surface 430 may be formed from non-continuous surfaces. In still other embodiments, a generally planar bottom wall 404 of base portion 402 may also define a support surface 430, without separately identifiable structures.

As shown in FIG. 11, piston guide portions 406 extend generally upward from bottom wall 402. Piston guide portions 406 define guide channels 408 which are sized to receive piston tabs 474. In the embodiment shown, two piston guide portions 406 are placed on opposite sides of annular opening 428. In other embodiments, additional piston guide portions 406 may be provided and define additional piston guide slots 408. In still other embodiments, a piston guide portion 406 may define multiple piston guide channels 408 and may partially or completely surround piston 470.

Piston 470 includes a generally cylindrical side wall 472 and a downwardly convex piston bottom surface 476. Piston 470 further includes at least one piston tab 474 having a tab bottom 478. In a preferred embodiment, piston 470 is provided with piston tab 474 and a second piston tab 474 placed on the opposite side of piston 470. Piston tabs 474 slidingly engage piston guide slots 408, thereby allowing vertical movement of piston 470.

Figure 13A:
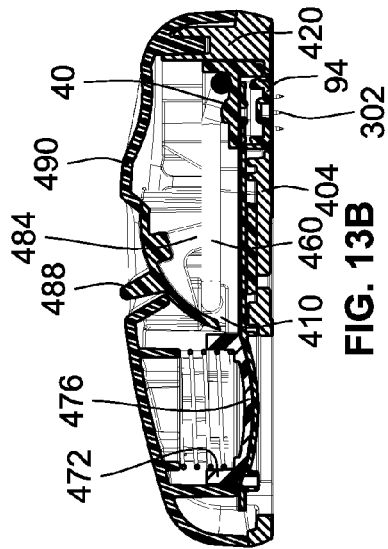
FIG. 13A is cross-sectional view along line 13A-13A of the second exemplary drug delivery device in an pre-activation position.
Figure 13B:
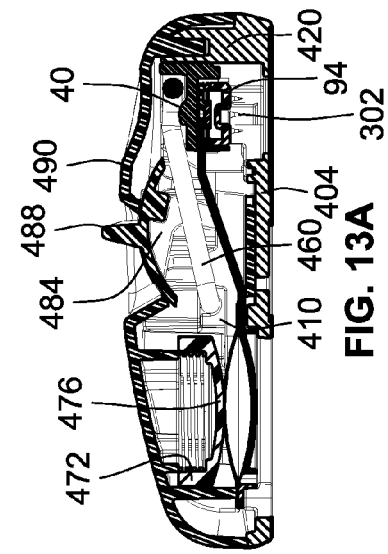
FIG. 13B is cross-sectional view along line 13B-13B of the second exemplary drug delivery device in an activated position.
Figure 14A:
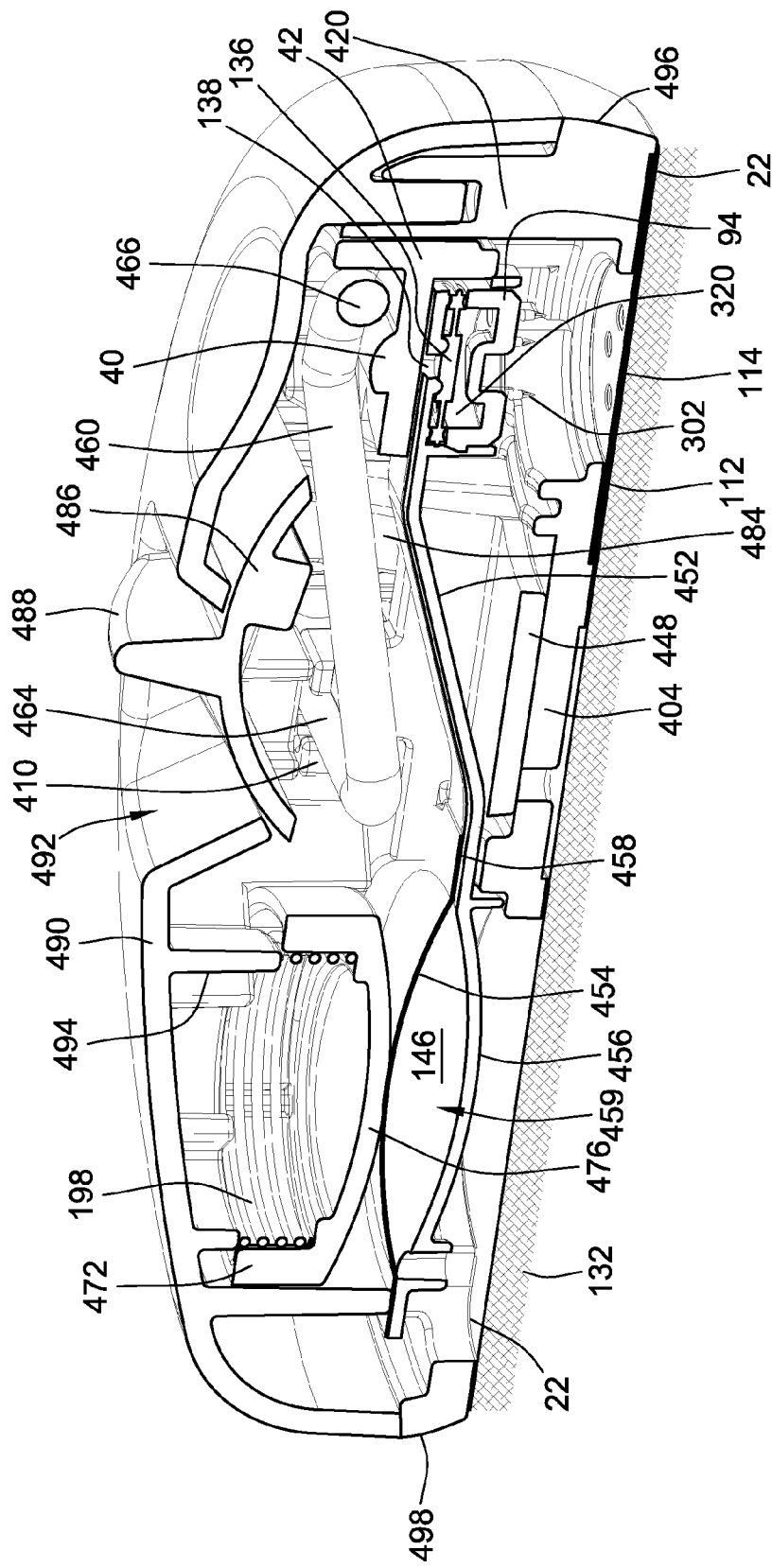
FIG. 14A is an isometric sectional view along line 13A-13A of the second exemplary drug delivery device in an pre-activation position.
Figure 14B:
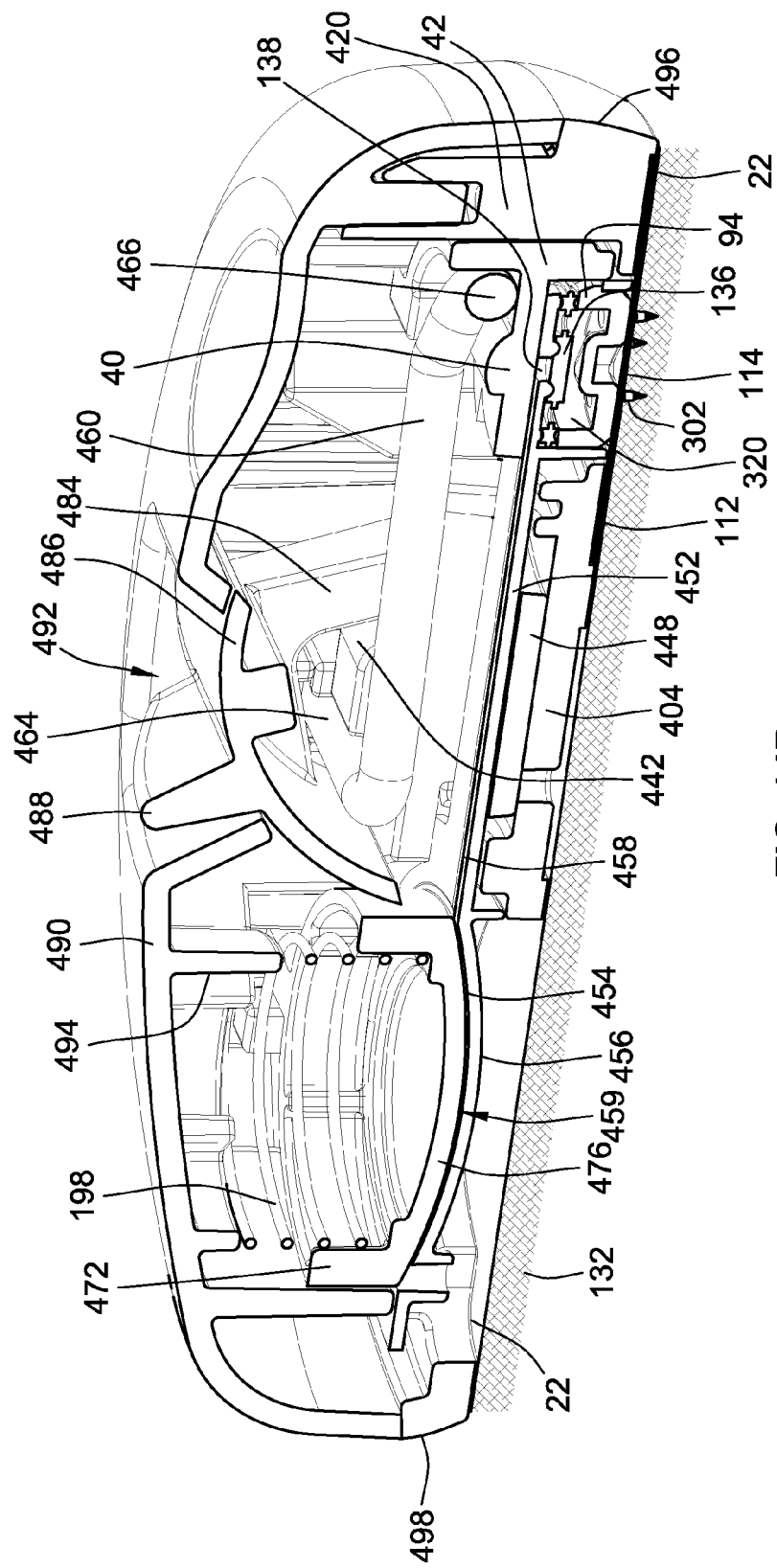
FIG. 14B is an isometric sectional view along line 13B-13B of the second exemplary drug delivery device in an activated position.

Also referring to FIGS. 13 and 14, drug delivery device 400 includes a reservoir actuator or force generating element, shown as piston spring 198. Piston spring 198 is positioned inside piston 470 in a compressed state to provide a downward motivating force against piston 470 when drug delivery device 400 is placed in an activated condition. Piston spring 198 is held in position by pillars 494, as best shown in FIGS. 14A and 14B.

Referring again to FIG. 11, spring support portions 410 of base portion 402 are provided with retention sockets 412. Retention sockets 412 receive and retain transverse portions 464 of torsion spring 460. Additionally, shuttle support portion 418 is provided with spring retention grooves 426. In the embodiment shown, spring retention grooves 426 are generally parallel to bottom wall 404. Spring retention grooves receive and retain fixed ends 462 of torsion spring 460.

Bottom wall 404 of base portion 402 includes fulcrum sockets 414. As shown, fulcrum sockets 414 are molded as depressions in bottom wall 404 of base portion 402. Fulcrum sockets 414 receive and retain pivot bosses 482 of activation lever 480, thereby permitting activation lever 480 to rotate about pivot bosses 482. Fulcrum sockets 414 may be further defined by fulcrum posts 416. In another embodiment, pivot bosses 482 may be engaged within a fulcrum post rather than within bottom wall 404 of base portion 402.

Shuttle support portion 418 is generally cylindrically shaped and extends upward from bottom wall 404. Shuttle support portion 418 includes a wall 420 defining an generally cylindrical central cavity 422. Central cavity 422 is sized to slidably receive shuttle 38. Shuttle 38 is provided with first guide arm 46 and second guide arm 48. Guide arms 46 and 48 are slidably received within channels 424 of shuttle support portion 418, when shuttle 38 is received in the center cavity 422 of shuttle support portion 418. Channels 424 act as a vertical movement guide for guide arms 46 and 48, to help ensure that shuttle 38 moves a generally linearly downward direction during activation of delivery device 400.

Bottom wall 404 may be provided with an opening to receive needle screen 112 having needle holes 114, and an adhesive layer 22. In another embodiment, needle holes 114 may be formed directly into bottom wall 404.

Drug delivery device 400 also includes a microneedle activation element or microneedle actuator, shown as, but not limited to, needle spring 460. As explained in greater detail below, needle spring 460 stores energy, which upon activation of drug delivery device 400, is transferred to one or more microneedles causing the microneedles to penetrate the skin. In other embodiments, other spring types, such as a coiled compression spring or leaf spring may instead be employed.

Shuttle 38 further includes a top wall 40 having a generally hemi-cylindrical top surface providing points of contact between top wall 40 and U-shaped portion 466 of needle spring 460. As needle spring 460 propels shuttle 38 downwards towards bottom wall 404, needle spring 460 rotates slightly about top wall 40, maintaining contact between U-shaped contact portion 466 and top wall 40. Shuttle 38 is also includes a generally cylindrically shaped shuttle wall or skirt 42. Skirt 42 is slidably received by central cavity 122. The bottom edge 43 of skirt 42 contacts the top surface of cup portion 94, described in further detail below.

Trigger element 440 includes and a pair of trigger arms 162, trigger fingers 444, and a generally planar trigger side walls 170. Trigger side walls 170 are connected via sliding base 448. The top edges of trigger side walls 170 include shuttle support rails 172 and lever bosses 442. Trigger element 440 is slidably received by base portion 402 such that sliding base 448 rests atop bottom wall 404 of base portion 402, and between guide rails 434 of base portion 402. Trigger fingers 444 include a top wall 446. Prior to activation of device 400, bottom surfaces 478 of piston tabs 464 are positioned in contact with top wall 446 of trigger fingers 444, thereby preventing downward motion of piston 470 in response to the force exerted by piston spring 198.

In the embodiment shown, device 400 includes a trigger lever 480. Trigger lever 480 includes pivot bosses 482, lever arms 484, arched top 486, and ridge 488. Pivot bosses 482 are received and retained by fulcrum sockets 414, thereby permitting trigger lever 480 to rotate about pivot bosses 482. Lever arms 484 are positioned to slidingly engage with lever bosses 442 as lever arms 484 of trigger lever 480 are rotated towards the rear 498 of device 400 during activation by a user.

In the pre-activation position, shuttle 38 is supported by shuttle support rails 172. U-shaped contact portion 466 of needle spring 460 bears against top contact cylinder 40 of shuttle 38, and exerts a downward force on shuttle 38. Shuttle support rails 172 thereby prevent the downward motion of shuttle 38 and microneedle array 300 when the device 400 is in an unactivated state.

Still referring to FIG. 11, drug delivery device 400 further includes a drug reservoir 450 including a reservoir base 456 and drug channel arm 452. The lower surface of drug channel arm 452 includes a depression or groove 458 that extends from reservoir base 456 along the length of drug channel arm 452. Drug reservoir 450 further includes a flexible barrier film 454 adhered to the inner surfaces of both drug reservoir base 456 and drug channel arm 452. Barrier film 454 is adhered to form a fluid tight seal or a hermetic seal with drug reservoir base 456 and channel arm 452. In this arrangement (shown best in FIGS. 14A and 14B), the inner surface of drug reservoir base 456 and the inner surface of barrier film 454 form a drug reservoir 459, and the inner surface of drug channel arm 452 and the inner surface of barrier film 454 form a fluid channel, shown as, but not limited to, drug channel 458. In this embodiment, drug channel arm 452 acts as a conduit to allow fluid to flow from drug reservoir 459, through opening 138 and check valve 136, and to microneedles 302 of microneedle array 300.

Referring to FIG. 14A, an isometric sectional view of delivery device 400 is shown attached or adhered to skin 132 of a subject prior to activation of the device. Delivery device 400 includes a microneedle component, shown as, but not limited to, microneedle array 300, having a plurality of microneedles, shown as, but not limited to, hollow microneedles 302, extending from the lower surface of microneedle array 300. In the embodiment shown, microneedle array 300 includes an internal channel 320 allowing fluid communication from the upper surface of microneedle array 300 to the tips or ports of hollow microneedles 302, shown in further detail below.

Delivery device 400 also includes a valve component, shown as, but not limited to, check valve 136. Both microneedle array 300 and check valve 136 are mounted within cup portion 94. Drug channel 458 terminates in an aperture or hole 138 positioned above check valve 136. In the pre-activation or inactive position shown in FIG. 14A, check valve 136 blocks aperture 138 at the end of drug channel 458 preventing a substance, shown as, but not limited to, drug 146, within drug reservoir 459 from flowing into microneedle array 300.

Referring to FIGS. 14A and 14B, to activate drug delivery device 400, a user applies a force against ridge 488 of trigger lever 480 in a direction towards rear 498 of device 400, thereby rotating trigger lever 480 about pivot bosses 482 and towards the rear 498 of drug delivery device 400. Trigger arms 484 thereby apply a rearward-directed horizontal force to lever bosses 442, and thereby translate trigger element 440 towards the rear 498 of drug delivery device 400 in a sliding motion.

As trigger element 440 slides towards the rear 498 of base 402, trigger fingers 444 slide from underneath piston tabs 474, thereby permitting piston 470 to move in a downward direction in response to the force provided by piston spring 198. Additionally, the sliding movement of trigger element 440 removes shuttle support rails 172 from their position directly below shuttle 38. Needle spring 460 thereby forces shuttle 38, needle cup 94, and microneedle array 300 downwards and inserts microneedles 302 into the skin of the subject. In the embodiment shown, trigger element 440 releases piston 470 and shuttle 38 at substantially the same time. In a preferred embodiment, needle spring 460 inserts the microneedles 302 of microneedle array 300 into the skin of the subject at a velocity of about 4 to 6 meters per second. In another embodiment, needle spring 460 inserts microneedles 302 at a velocity between about 6 to 12 meters per second. In still another embodiment, needle spring 460 inserts microneedles 302 at a velocity between about 2 to 4 meters per second.

As piston spring 198 uncompresses, piston 470 is moved downward and forces barrier film 454 downward toward drug reservoir base 456. As barrier film 454 is pushed downward by piston 470, pressure within drug reservoir 459 and drug channel 458 increases. When the fluid pressure within drug reservoir 459 and drug channel 458 reaches a threshold, check valve 136 is forced open allowing drug 146 within drug reservoir 459 to flow through aperture 138 at the end of drug channel 458. As shown, check valve 136 includes a plurality of holes 140, and microneedle array 300 includes a plurality of hollow microneedles 302. Drug channel 458, aperture 138, plurality of holes 140 of check valve 136, internal channel 320 of microneedle array 300 and hollow microneedles 302 define a fluid channel between drug reservoir 459 and the subject when check valve 136 is opened. Thus, drug 146 is delivered from reservoir 459 through drug channel 458 and out of hollow microneedles 302 to the skin of the subject by the pressure generated by piston spring 198.

Microneedles

When a needle is inserted into the skin or tissue of a patient at a point of entry, tissue proximate to the tip region is compressed in a volume designated the tissue compression zone. The compression of tissue at the needle tip hinders delivery of fluids into the tissue compression zone, requiring a higher delivery pressure to effectuate fluid delivery. Tissue spatially removed from the tip and proximal to the needle is less compressed, and is known as the fluid infusion zone.

Additionally, tissue near the needle's point of entry, designated the tissue sealing zone, exerts a force against the needle directed approximately radially inward, helping to seal the opening in the skin and prevent escape of fluid back through the opening in the skin of the patient. This sealing effect may be amplified by providing a needle having a diameter that is tapered from a larger diameter at the needle base to a smaller diameter at the needle tip. The sealing effect may be further amplified by providing a flare at the base of the microneedle.

Fluid delivery into the infusion zone requires a lower delivery pressure for an equivalent fluid delivery rates when compared to fluid delivery into the tissue compression zone. It is therefore desirable to administer fluids to the infusion zone. Additionally, fluid delivery into the infusion zone causes less trauma to the tissue receiving the fluid, therefore resulting in a lesser perception of sensation or pain to the patient as fluids are delivered.

A convention medical needle, or hypodermic needle, comprises a shaft having an outer diameter; a lumen, or central channel, coaxial to the shaft and having an interior diameter; and a tip or point. A conventional medical needle is typically provided with a regular medical point, having a tip angle of about 15 degrees to the longitudinal axis of the needle shaft. The tip and shaft define a lumen opening that permits fluid communication between the lumen and tissues of a patient.

When a conventional medical needle is inserted into tissue, the portion of the lumen opening closest to the tip is in the tissue compression zone, while a portion of the lumen opening distal to the tip is in less-compressed tissue. Accordingly, a fluid may be delivered through central lumen into the fluid infusion zone in a needle where the lumen opening is positioned at the tip of the needle.

Referring to FIG. 9A, a microneedle array 300 is shown according to one embodiment. Microneedle array 300 includes one or more microneedles 302. Referring to FIG. 9B, microneedle array 300 is shown with an array base 310 having a generally cylindrical wall 316 and a bottom plane 318, together defining a internal channel 320.

Referring to FIGS. 9C and 9D, microneedle 302 is shown having a tip portion 304, a shaft portion 306, and a base portion 308. Microneedles 302 include a center lumen or cavity 312, and also include one or more side port openings 314. Side port openings 314 are in fluid communication with lumen 312. Side ports 314 are placed below tip portion 304, such that side ports 314 are in fluid communication with the fluid infusion zone when microneedles 302 are inserted into a patient's dermis. In a preferred embodiment, microneedles 302 are provided with three side port openings 314 spaced equidistantly around the perimeter of microneedle 302. In other embodiments, microneedles may be provided with one, two, or four or more openings. Side port openings 314 may be formed by casting methods as is known in the art, or may be formed by the removal of material from microneedle 302 after microneedle 302 is formed.

As shown, shaft portion 306 may be formed with a taper such that the shaft diameter decreases distal to array base 310. In another embodiment, shaft portion 306 may have parallel sides. Shaft portion 306 extends from array base 310 to the bottom of side port openings 314. Shaft portion 306 may be further provided with a flare at base 308. Base flare 308 may provide an additional sealing effect at the skin of the patient when inserted into the skin.

Microneedles 302 are shown integrally formed with array base 310. However, in other embodiments microneedles 302 may be formed separately from array base 310 and affixed to array base 310. In a preferred embodiment, microneedle 302 has an overall height of about 0.069 inches, including a shaft height of about 0.035 inches, a side port height of about 0.020 inches, and a height of about 0.013 inches from the top of the side ports to the point of tip 304. In other embodiments, microneedle 302 may have a height of about 0.060 inches, about 0.080 inches, about 0.100 inches, or 0.120 inches or greater. As shown, tip portion 304 has an internal angle at the point of about 30 degrees. In other embodiments, tip portion 304 may have a point angle of about 25 degrees to about 35 degrees, or may have a point angle of about 20 degrees to about 40 degrees.

In a preferred embodiment, microneedle array is provided with 6 microneedles 302. However, microneedle array may be provided with fewer needles (i.e., one, two, three to five) or more needles (i.e. eight, ten, or twelve or more needles). In a preferred embodiment, microneedles 302 are regularly spaced on array base 310.

In a preferred embodiment, microneedle array 300 is provided with installation tabs 326. Installation tabs are received by complementary openings in needle cup 94, as shown in FIG. 2. Installation tabs 326 may be received by openings 95 in needle cup 94, thereby securing the microneedle array 300 into needle cup 94 and facilitating installation. In a preferred embodiment, microneedle array is also provided with a tool interface recess 324, shown as a triangular indentation in bottom plane 318. Tool interface recess 324 is configured to be compatible with automated component handling machinery, to permit automated placement of microneedle arrays into drug delivery devices during a manufacturing process.

In some embodiments, microneedle arrays are formed from a plastic material. In a preferred embodiment, microneedle arrays are injection molded as a single piece using a liquid crystal polymer (LCP). In other embodiments, microneedle arrays 300 may be molded from ceramics, resins, metals, etc. In still other embodiments, microneedle arrays may be formed by a subtractive process, for example silicon etching or micromachining techniques, to remove undesired material from a block of starting material.

Figure 10:
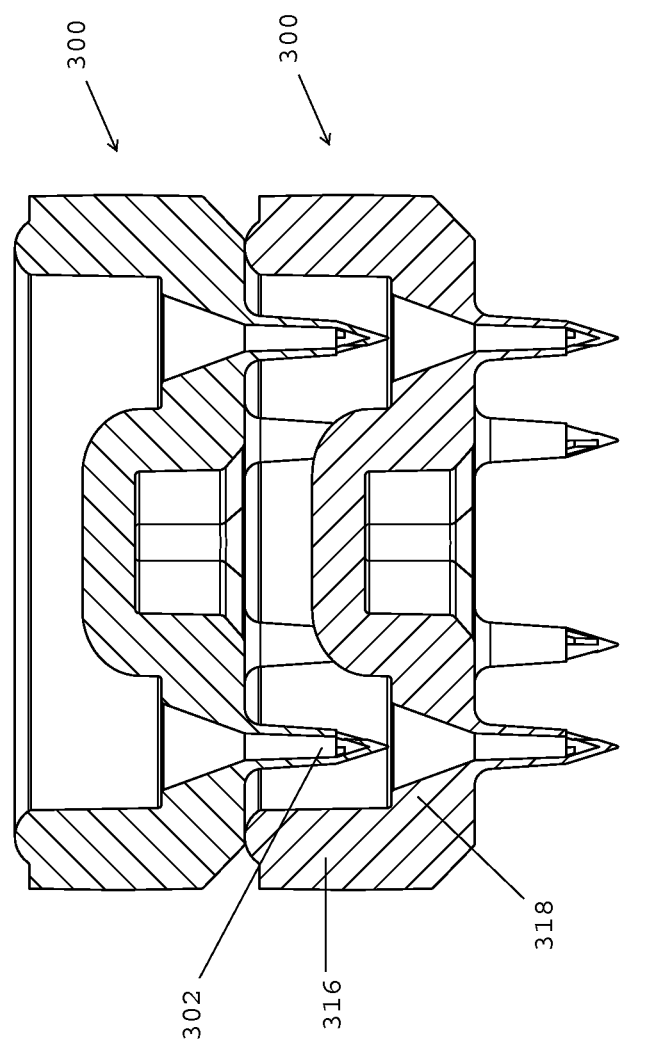
FIG. 10 is a side cross-sectional view of stacked microneedle arrays.

Referring to FIG. 10, microneedle arrays 300 may be stacked in a vertical arrangement for packaging and transport, thereby protecting individual microneedles 302 from impact or contact with other surfaces. As shown in FIG. 10, wall 316 is formed with a height such that the depth of internal channel 320 is greater than the height of microneedles 302. Accordingly, when a first microneedle array is coaxially positioned in vertical contact with a second microneedle array, the individual microneedles of the first array do not contact the bottom plane 318 of the second microneedle array, regardless of the rotational orientation of the microneedle arrays with respect to each other. Stacked microneedle arrays may be enclosed in a tubular packing format for transportation and automated assembly into a drug delivery device.

Further modifications and alternative embodiments of various aspects of the invention will be apparent to those skilled in the art in view of this description. Accordingly, this description is to be construed as illustrative only. The construction and arrangements of the drug delivery device, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A drug delivery device for delivering a drug to a subject having a skin surface, the device comprising:
 a base portion for resting on the skin surface;
 a drug reservoir supported by the base portion, the reservoir containing the drug;
 at least one hollow microneedle having a tip portion for penetrating the skin of the subject and in fluid communication with the reservoir;
 a first stored energy mechanism releasable to force the tips into the skin;
 a second stored energy mechanism releasable to force drug from the reservoir through the needle; and
 a trigger slideably supported by the base portion and coupled to the first and second stored energy mechanisms to release the mechanisms such that the tip is forced into the skin before the drug is forced through the needle.

2. The device of claim 1, wherein the hollow microneedle is a side port microneedle, and wherein the side ports are positioned on the hollow microneedle to be in fluid communication with a fluid infusion zone.

3. The device of claim 1, wherein the microneedle has a plurality of side ports.

4. The device of claim 1, wherein the trigger is actuated by translation of an activation button, wherein the activation button is translated in a direction substantially parallel to the base portion of the device.

5. The device of claim 1, wherein the trigger is actuated by rotation of an activation lever, wherein the activation lever translates the trigger in a direction substantially parallel to the base portion of the device.

6. The device of claim 1, wherein the device further comprises a microneedle array having a plurality of microneedles.

7. The device of claim 1, wherein the trigger is further moveable to place the hollow microneedle into a retracted position.

8. The device of claim 1, wherein the device comprises a window providing a visual indication of the completion of drug delivery.

9. A drug delivery device for delivering a drug to a subject having a skin surface, the device comprising:
- a base portion for resting on the skin surface, wherein the base portion has a substantially planar bottom wall defining a bottom plane;
- a drug reservoir supported by the base portion, the reservoir containing the drug;
- at least one hollow microneedle having a tip portion for penetrating the skin of the subject and in fluid communication with the reservoir during drug delivery;
- a first stored energy mechanism releasable to force the tips into the skin;
- a second stored energy mechanism releasable to force drug from the reservoir through the needle; and
- a trigger slideably supported by the base portion and coupled to the first and second stored energy mechanisms to release the mechanisms such that the tip is forced from a position above the bottom plane to a position below the bottom plane before the drug is forced through the needle.

10. The drug delivery device of claim 9, wherein the plurality of hollow microneedles are between about 0.060 inches to 0.080 inches in height.

* * * * *